United States Patent
Satterfield

(10) Patent No.: US 6,179,804 B1
(45) Date of Patent: Jan. 30, 2001

(54) TREATMENT APPARATUS FOR WOUNDS

(75) Inventor: Elaine T. Satterfield, Jackson County, GA (US)

(73) Assignee: Oxypatch, LLC, Gainesville, GA (US)

( * ) Notice: Under 35 U.S.C. 154(b), the term of this patent shall be extended for 0 days.

(21) Appl. No.: 09/376,916

(22) Filed: Aug. 18, 1999

(51) Int. Cl.$^7$ .................................................. A61M 37/00
(52) U.S. Cl. ............................ 604/23; 604/305; 604/307; 604/290
(58) Field of Search ................................ 604/290, 23–25, 604/305, 289, 304, 307, 306; 128/118.1, 202.12, 121.1, 24.1, 125.1

(56) References Cited

U.S. PATENT DOCUMENTS

| | | |
|---|---|---|
| 2,998,817 | 9/1961 | Armstrong . |
| 3,089,492 | 5/1963 | Owens . |
| 3,467,081 | 9/1969 | Glass . |
| 3,610,238 | 10/1971 | Rich, Jr. . |
| 3,920,006 | 11/1975 | Lapidus . |
| 4,182,329 | 1/1980 | Smit et al. . |
| 4,224,941 | 9/1980 | Stivala ............................ 128/207.26 |
| 4,328,799 | 5/1982 | LoPiano . |
| 4,474,571 | 10/1984 | Lasley . |
| 4,480,638 | 11/1984 | Schmid . |
| 4,509,513 | 4/1985 | Lasley . |
| 4,608,041 | 8/1986 | Nielsen ................................... 604/23 |
| 4,685,447 | 8/1987 | Iversen et al. . |
| 4,778,446 | 10/1988 | Jensen . |
| 4,801,291 | 1/1989 | Loori . |
| 4,969,881 | 11/1990 | Viesturs ............................... 604/305 |
| 5,154,697 | 10/1992 | Loori ..................................... 604/23 |
| 5,662,625 | 9/1997 | Westwood ........................... 604/305 |

*Primary Examiner*—Sharon Kennedy
*Assistant Examiner*—Deborah Blyveis
(74) *Attorney, Agent, or Firm*—Holland & Knight LLP; David G. Maire; James H. Beusse

(57) ABSTRACT

An apparatus 101 for applying treatment gas to a wound, burn, infection or otherwise damaged skin area comprises an inflatable dome 103 attached to the surrounding skin portion 105 by a seal gasket 107. An age-degradable adhesive 215 seals and attaches the seal gasket to the surrounding skin portion. A re-sealable adhesive 213 releasable attaches the dome to the seal gasket. A treatment gas hose 109 and nozzle 111 provide treatment gas to the interior portion 107 enclosed by the inflatable dome. Stimulator electrodes 117, attached to the apparatus provide electrical stimulation to skin portions 105A surrounding the wound area, which together with the treatment gas, promote healing of the wound. The re-sealable adhesive allows quick and easy removal and reapplication of the inflatable dome without removal of the seal gasket.

29 Claims, 3 Drawing Sheets

TREATMENT APPARATUS FOR WOUNDS

BACKGROUND OF THE INVENTION

The present invention relates to medical devices, and, more particularly, to medical devices for the promotion of healing wounds, burns and infections.

Use of oxygen to promote healing of wounds, burns, and infections has been documented. Nielsen discloses a device for treatment of wounds by exposure to jets in U.S. Pat. No. 4,608,041. A series of inlet and outlet openings ventilate a space between the device and the wound area. The device is fixed over the area of the wound by means of plaster or tape.

Loori discloses a collapsible topical hyperbaric apparatus in U.S. Pat. No. 5,154,697. A gas inlet tube introduces oxygen to a shell covering the treated area. An adhesive sealing ring on the bottom of the unit secures the device to the affected area in conjunction with a belt.

These and other devices, while providing a chamber to apply oxygen to a wound, are difficult to apply, remove and re-apply. The previous devices are sometimes ineffective in particularly difficult-to-heal wounds.

OBJECTS AND SUMMARY OF THE INVENTION

Therefore an object of the present invention is to provide a device which supplies treatment gas to a wound, burn or infection which is easily and quickly removable and replaceable over the affected area.

A further object of the present invention is to provide a device which supplies treatment gas to a wound which promotes circulatory action in order to promote healing.

Another object of the present invention is to provide a treatment device and method of use, which provides effective treatment of wounds not previously achieved with treatment gas application.

Yet another object of the present invention is to provide a device which supplies treatment gas to a wound which is simple to use and low in cost.

Surprisingly, it has been found that simultaneous application of a treatment gas such as oxygen to a wound while simultaneously providing electrical stimulus to the area between the blood supply and the wound promotes especially fast healing. The method also promotes healing of wound areas not responsive to other forms of treatment. Wounds, burns and infections which have been unresponsive to treatment gas application alone are responsive when subjected to both treatment gas and electrical stimulation in adjacent areas. This is especially the case with electrical stimulation in the area between the blood supply and the wound. Timed applications of treatment gas spaced over periods of ambient conditions further promotes healing in difficult cases. The apparatus of the present invention comprises a treatment gas applicator including a treatment gas supply portion, a treatment gas containment portion, and a gas vent portion. In its preferred embodiment, the apparatus also comprises at least two electrodes attached to the treatment gas applicator to provide electrical stimulation of nearby areas in order to promote blood supply to the wound area. In a preferred embodiment, the apparatus includes a seal gasket which remains attached to the surrounding area of the wound and allows quick and simple removal and replacement of the treatment gas containment portion of the apparatus. The apparatus is secure without the use of straps and eternal securing devices. The seal gasket is easily removable from the affected area without pain or damage to the wound area upon completion of use of the apparatus.

One embodiment of the present invention the treatment gas containment portion is an inflatable dome attached to the surrounding area of the wound by a seal gasket. In the preferred embodiments, the inflatable dome is made of a flexible membrane to reduce pressure on the wound area if bumped by an object, and to reduce storage space when not in use. The lower seal surface of the seal gasket comprises an age-degradable adhesive. The age-degradable adhesive adheres and seals the seal gasket to the surrounding skin.

The upper seal surface of the seal gasket comprises a releasable adhesive such as a pressure-sensitive adhesive. The releasable adhesive adheres and seals the upper seal surface of the seal gasket to a lower seal surface of the inflatable dome.

The age-degradable adhesive is more substantial and permanent as compared to the re-sealable adhesive. As a result, a user easily removes and replaces the inflatable dome on the seal gasket, and the seal gasket remains in place on the surrounding skin portion for all or a significant portion of the healing time of the wound. This allows removal and replacement of the inflatable dome for treatment periods as determined by a physician. It also allows easy removal for cleaning and dressing of the wound. The residence time of the seal gasket on the surrounding skin portion is typically several days and, in some cases five or ten days depending on the age-degradable adhesive qualities and environmental conditions. Upon end of life of the age-degradable adhesive, the user easily removes the seal gasket without pain or damage to the surrounding skin portion.

In a preferred embodiment, the treatment gas supply portion includes a supply hose and nozzle, supplying a treatment gas such as oxygen to the interior portion of the inflatable dome. One or more vents in the membrane forming the inflatable dome provide a predetermined restriction of venting of exhaust gasses from the interior portion. The restricted venting maintains inflation of the dome when a predetermined flow of oxygen is supplied to the dome. The vents also allow removal of off-gasses from the wound. A mesh or fabric layer over the membrane acts as a filter layer and allows escape of the vented exhaust gas while preventing entrance of foreign material into the interior portion. A sterile fabric or mesh material, optionally bonded on the inner surface of the inflatable dome, prevents contact of the flexible membrane with the wound.

In the preferred embodiments, at least one pair of electrodes attached to the apparatus provide stimulation of blood supply to the wound area. In one embodiment, a pair of stimulator electrode patches are attached to the oxygen supply hose by insulated electrical conductors. The conductors terminate at electrical plugs attached to the hose. The electrode attachment method provides a reminder to the user to attach the electrodes, and the location and length of the electrode conductors provides guidance to proper positioning of the electrodes relative to the wound.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

The following is a description of the preferred embodiments of a treatment apparatus for promoting healing of a wound.

Figure 1:
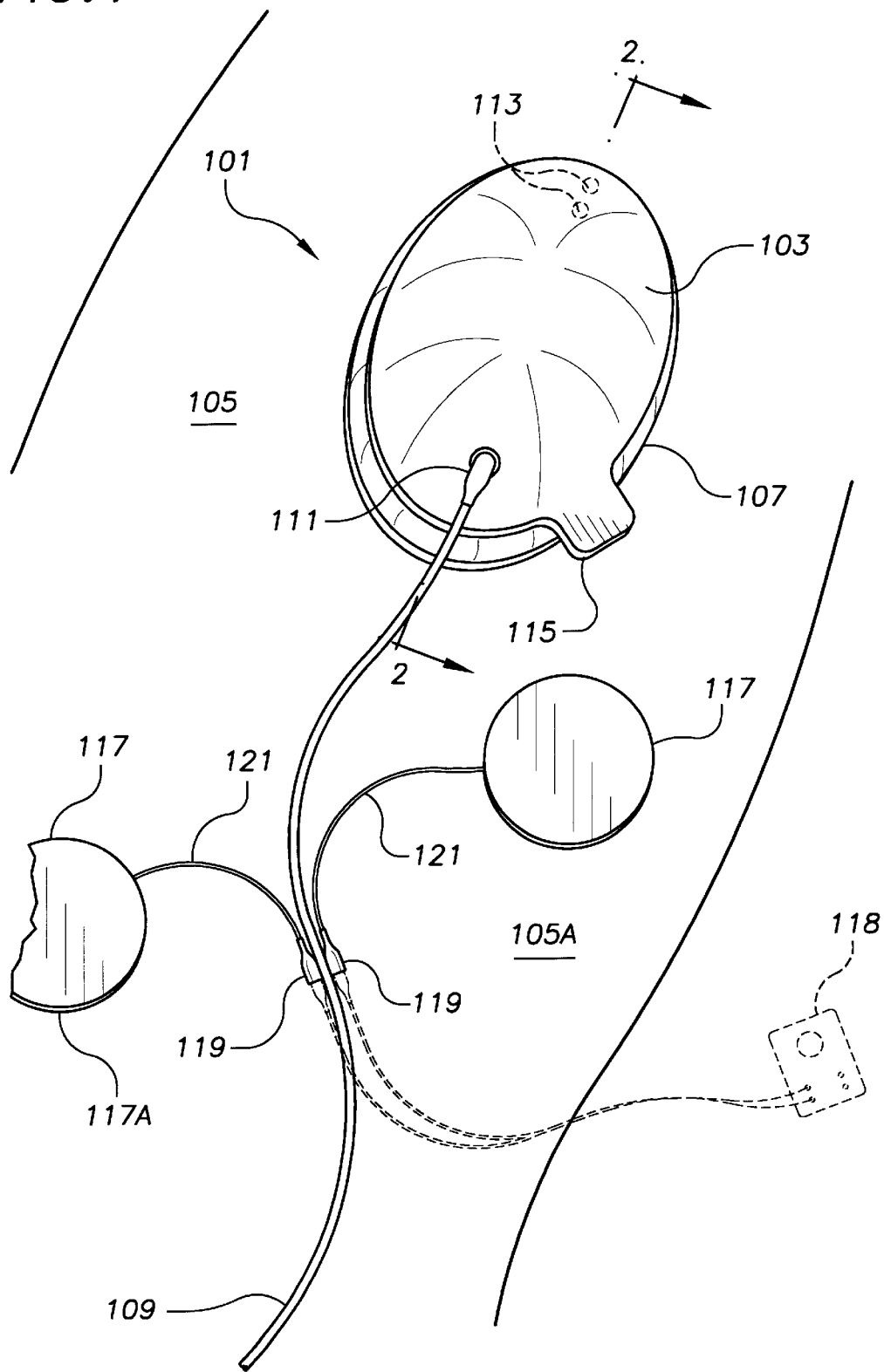
FIG. 1 is a perspective drawing of an embodiment of oxygen application apparatus showing an inflatable dome attached to a skin portion surrounding a wound by a seal gasket, and two stimulation electrodes attached to an oxygen supply hose.
Figure 2:
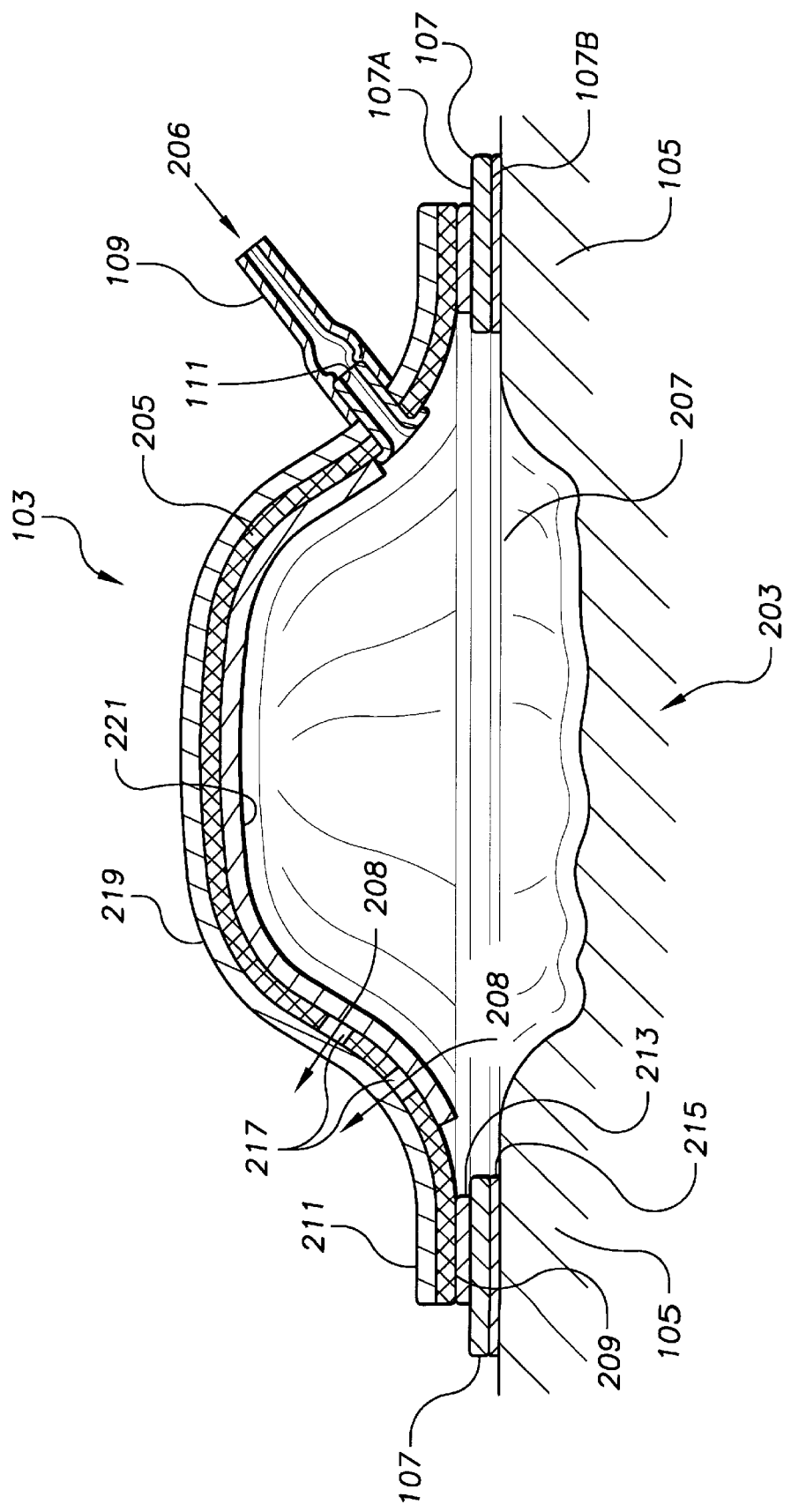
FIG. 2 is a cross section of the inflatable dome and seal gasket taken along lines 2—2 of FIG. 1.

FIG. 1 is a perspective drawing of treatment apparatus 101 covering a wound area (203 of FIG. 2). The apparatus consists of an inflatable dome portion 103 attached to surrounding skin portion 105 by seal gasket 107. Oxygen supply hose 109 supplies oxygen to inflatable dome 103 through fitting or nozzle 111. Gas vents 113 vent gasses inside dome 103 to atmosphere. Tab 115 promotes removal of dome portion 103 from seal gasket 107.

Electrical stimulation electrodes such as electrode patches 117 provide electrical connections to surrounding skin portion 105A to promote blood supply to the wound area and further promote healing. A power supply 118 supplies electric current to electrode patch 117 through plugs 119 and current carrying conductors or wires 121. Plugs 119 are attached to oxygen supply hose 109 by adhesives, welding, or mechanical connectors. Alternatively, plugs 119 are connected to dome portion 103. A contact adhesive attached to the bottom 117A of electrode patches 117 attach the patches to surrounding skin portion 105A.

FIG. 2 is a cross section drawing of inflatable dome portion 103 taken along lines 2—2 of FIG. 1. Membrane 205 is a flexible gas barrier providing the structure of dome portion 103 when inflated by a gas such as oxygen. In the preferred embodiment, membrane 205 is made of a polymeric sheet or film such as polyolefin film. Other materials include PVC, fluoropolymers, and natural and synthetic rubber sheets and films. In alternative embodiments, membrane 205 is a rigid or semi-rigid material such as plastic, formed in a dome shape. Dome peripheral portion 211 may be the peripheral portion of membrane 205, or it may be a ring-shaped element bonded by adhesives, welding, or fasteners to membrane 205. In the preferred embodiments, peripheral portion 211 is flexible to provide sealing with seal gasket 107 on uneven portions of the body.

Oxygen supply hose 109 provides oxygen flow 206 to dome interior portion 207 through nozzle 111 inserted through an aperture in membrane 205. Nozzle 111 is sealed and attached to membrane 205 by adhesives, welding or mechanical fasteners. Gasket 107 seals interior portion 207 of inflatable dome 103 against wound area 203 and surrounding skin portion 105. In the preferred embodiments, gasket 107 is a ring-shaped flexible member made of a hypoallergenic polymer material such as MicroSkin available from Cymed.

In the preferred embodiments, upper gasket surface 107A of seal gasket 107 and lower dome seal surface 209 of dome peripheral portion 211 are releasable and re-sealable with respect to each other. In one preferred embodiment, the releasable and re-sealable feature of surfaces 107A and 209 are provided by a releasable and re-sealable contact adhesive 213 fixed to surface 107A. Lower dome seal surface 209 is a smooth seal surface to which adhesive 213 releasably seals surface 107A. Alternatively, adhesive 213 is fixed to lower dome seal surface 209 and adhesive 213 is releasable and re-sealable to surface 107A. Adhesive 213 may be a pressure sensitive adhesive. The releasable (non-adhesive) surface may be treated to promote release from the releasable adhesive.

A second adhesive 215 attaches seal gasket 107 to surrounding skin portion 105. Adhesive 213 is a controlled degradable adhesive. In the preferred embodiments, second adhesive 215 is an age-degradable, septic and hypoallergenic adhesive. For the purposes of this disclosure, and age-degradable adhesive is one in which the adhesive capability with the skin decreases with time, either from a direct time dependent process, or a process in which time not an direct, but rather a substantial indirect, factor in the adhesive degradation process. The preferred time periods of degradability are those typical for wound healing, i.e. 3–14 days.

The age-degradable feature may be provided by a hydrocolloid adhesive such as Duoderm, available from Conva-Tec. Hydrocolloid-based adhesives maintain adhesion to the skin until moisture saturation of the hydrocolloid component (typically 3–12 days, depending on hydrocolloid content and skin, wound and environmental conditions). The moisture saturation is age or time dependent in that moisture provided to the hydrocolloid component from the wound portion, the surrounding portion, and atmospheric moisture is cumulative with time.

Utilization of an age-degradable adhesive permits secure fastening of seal gasket 107 to surrounding skin portion 105 for a substantial period of time and sufficient for normal use of the apparatus. Upon age degradation of the adhesive, removal of seal gasket 107 is simple and painless, and completed without damage to the surrounding skin portion. In the preferred embodiments, adhesive 215 is attached to lower surface 107B of seal gasket 107.

Restricted discharge of gasses 208 through vents 217 of membrane 205 maintains inflation of interior portion 207 and provides ventilation of gasses discharged from wound area 203. Vents 217 provide restriction of gas entrapped in interior portion 207, resulting in a positive pressure in portion 207. Positive pressure provides the dome shape of membrane 205. Vents 217 may comprise one or more apertures in membrane 205 such as holes, slots, or perforations. Outer layer 219, made of a fabric, mesh or perforated material such as a fine polymeric mesh material, prevents introduction of foreign material into vents 217 while allowing, escape of gasses exiting, the vents. Outer layer 219 may be bonded to membrane 205 by adhesives, welding or fasteners.

Figure 3:
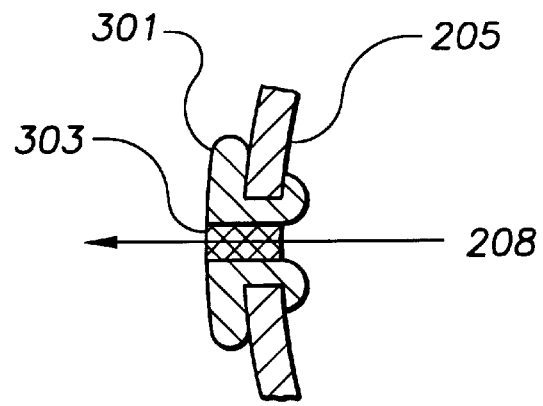
FIG. 3 is a detail cross section of a vent installed in the membrane of the inflatable dome of the apparatus.

FIG. 3 is a detail drawing of an alternative vent utilizing vent insert 301 attached to membrane 205. Vent 301 may be made of a polymeric, ceramic or metallic material. A contamination barrier or vent filter 303 allows venting of gasses 208 inside membrane 205 while preventing foreign material from entering, vent 301. Filter 303 may be made of natural or synthetic fiber material, or sintered metal or ceramic materials.

Referring back to FIG. 2, an inner layer 221 of a sterile material such as sterile gauss may be bonded to the inner side of membrane 205. Inner layer 221 may be a natural or synthetic woven, non-woven or mesh material, or, other dressing materials known in the art. Inner layer 221 prevents membrane 205 from sticking to wound area 203. In the preferred embodiments, inner layer 221 is a breathable material, allowing covering of vents 217 and/or nozzle 111 and yet permitting flow of treatment gas into interior portion 207 and gasses out of interior portion 207. In other embodiments, cutouts or positioning of inner layer 221 prevents covering of vents 217 and/or nozzle 111.

In use, seal gasket 107 is attached to surrounding skin portion 105 surrounding wound area 203, utilizing an adhesive such as age-degradable adhesive 215. A skin preparation agent may be used to remove contaminates from the skin and provide a thin protective film before application of the age-degradable adhesive. Removal of a peel strip (not shown) exposes releasable adhesive 213 on upper gasket surface 107A. Releasable adhesive 213 bonds lower dome seal surface 209 of inflatable dome 103 to seal gasket 107. The user removes peel strips (not shown) from electrode patches 117 and applies to surrounding skin portion 105A. Surrounding skin portion 105A is preferably upstream from a blood supply in relation to the wound so that the electrode patches will promote blood supply to wound area 203 upon energizing the patches.

Attachment of plugs 119 to supply hose 119 promotes correct use of the electrode patches since the physical attachment of the patches to the apparatus reminds the user to use and connect them. The placement of plugs 119 and the length of wire 121 promotes placement of the patches near the wound area where they are most effective. In alternative embodiments, additional electrode patches are attached to the apparatus.

Once dome portion 103 and electrode patches 117 are in place, the operator attaches oxygen hose 109 to a supply of oxygen, and stimulator power supply 118 to plugs 119. The operator then activates the oxygen supply and stimulator power supply 118.

Upon completion of the therapy, the operator may remove the dome portion by separating lower seal surface 209 of dome portion 103 from upper seal surface 107A. Tab 115 eases removal of dome portion 103. Re-sealable adhesive 213 allows removal and replacement of dome portion 103 without damage to the seal. In an alternative embodiment, a peel strip protects upper seal surface 107A when dome portion 103 is removed. Seal gasket 107 remains in place for several installations and removals of dome portion 103. Upon removal of dome portion 103, the wound may be cleaned or dressed or treated as directed.

Figure 4:
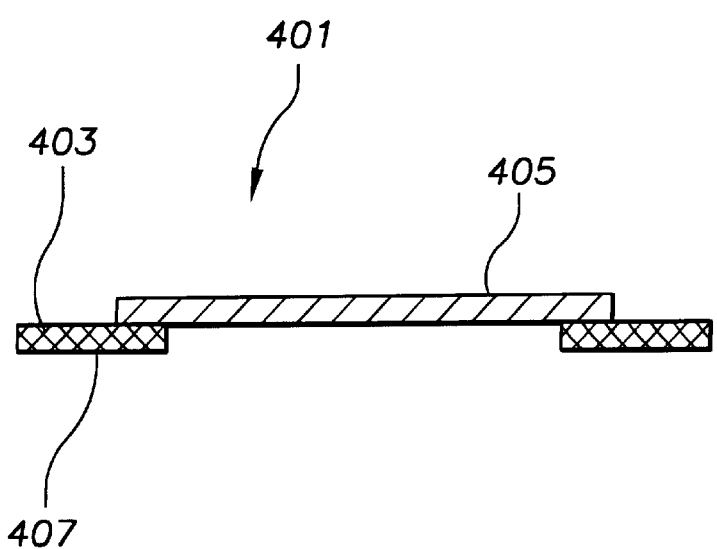
FIG. 4 is a cross section drawing of a dressing cover used in conjunction with the seal gasket of FIG. 1.

The wound may be covered by conventional dressings, or a dressing cover as shown in FIG. 4. Dressing cover 401 comprises a peripheral portion 403 of flexible material such as a polyolefin ring. A sterile dressing 405 covers the opening in peripheral portion 403. An adhesive bonds sterile dressing 405 to peripheral portion 403. Lower dressing seal surface 407 is sealable to upper seal gasket surface 107A.

In other embodiments, re-sealable adhesive 213 is fixed to dome lower seal surface 209 and lower dressing seal surface 407. The adhesive may be protected by a peel strip. In still other embodiments, oxygen nozzle 111 position provides physical stimulation of the wound by direct impingement of the gas on the wound area. Several nozzles placed to direct gas on the wound area provide additional stimulation. In still other embodiments, inflatable dome 103 may have other shapes such as rectangular, oval or octagonal.

Accordingly the reader will see that the TREATMENT APPARATUS FOR WOUNDS disclosed and claimed provides improved apparatus and methods for treating wounds. The apparatus provides the following additional advantages:

Simultaneous application of oxygen to the wound and promotion of circulation afforded by the electrode patches provides an apparent synergetic effect to rapidly heal difficult wounds;

Use of a re-sealable adhesive on the seal gasket allows the inflatable dome to be removed and replaced frequently and easily, and with low cost;

Placement of the electrode patches on the device reminds the user to connect them and place them correctly; and Use of an age-degradable adhesive on the seal gasket allows simple and painless removal upon completion of use.

Although the description above contains many specifications, these should not be construed as limiting the scope of the invention but as merely providing illustrations of some of the presently preferred embodiments of this invention. For example, mechanical fasteners may attach the dome portion to the seal gasket. A re-sealable adhesive may be used on the lower dome seal surface and the device used without a seal gasket. Or, the inflatable dome may be made of a rigid material.

Thus the scope of the invention should be determined by the appended claims and their legal equivalents, rather than by the examples given.

I claim:

1. A treatment gas application apparatus for a wound comprising:

a treatment gas containment portion comprising a containment peripheral portion, the containment peripheral portion comprising a first re-sealable seal surface on a bottom surface of the peripheral portion;

a seal gasket comprising an upper gasket peripheral portion and a lower gasket peripheral portion, the upper gasket peripheral portion comprising a second re-sealable seal surface and the lower gasket peripheral portion comprising a controlled-degradation adhesive, the controlled-degradation adhesive attachable to a skin portion surrounding the wound and degradable to promote removal of the seal gasket from the skin portion after a predetermined time;

a treatment gas Supply fitting attached to the treatment gas containment portion; and at least one exhaust vent in the treatment gas containment portion;

wherein the treatment gas containment portion and the seal gasket define a treatment gas ventilated space surrounding the wound when the lower gasket peripheral portion is attached to the surrounding skin by the controlled-degradation adhesive and the first resealable seal surface of the treatment gas containment portion is attached to the second resealable seal surface of the seal gasket.

2. The apparatus of claim 1 wherein the treatment gas containment portion comprises a flexible membrane and the vent is at least one aperture in the membrane sized to provide a predetermined restriction in exhaust vent flow wherein the flexible membrane forms an inflatable dome when the treatment gas containment portion is supplied by a predetermined flow of treatment gas through the treatment gas supply fitting.

3. The apparatus of claim 2 wherein said at least one vent comprises a filter allowing flow of ventilated gas through the vent and preventing foreign material from entering the dome.

4. The apparatus of claim 2 wherein the treatment gas containment portion comprises an outer layer of a gas permeable filter material outside the membrane.

5. The apparatus of claim 4 wherein the outer layer is a mesh material.

6. The apparatus of claim 4 wherein the treatment gas containment portion comprises an inner layer of a sterile dressing material.

7. The apparatus of claim 6 wherein the inner layer is a sterile gauze material.

8. The apparatus of claim 1, further comprising:

at least two current carrying conductors adapted for contact with the skin surrounding the wound at a first end and for connection to a power supply at a second end;

the at least two current carrying conductors being attached to the treatment gas containment portion so that the first end remains within a predetermined length of the treatment gas ventilated space.

9. The apparatus of claim 1, further comprising a tab attached to the containment peripheral portion.

10. A wound treatment apparatus for promoting healing of a wound comprising:
  a treatment gas applicator comprising a treatment gas containment portion attachable to a skin portion surrounding the wound and a treatment gas supply portion attached to the containment portion for supplying treatment gas to the containment portion; and
  at least two electrodes attachable to an adjacent skin portion of the wound, said at least two electrodes attached to the treatment gas applicator.

11. The apparatus of claim 10 wherein each of said at least two electrodes is attached to the treatment gas containment portion by a current carrying conductor.

12. The apparatus of claim 10 wherein each of said at least two electrodes is attached to the treatment gas supply portion by a current carrying conductor.

13. The apparatus of claim 12 wherein the treatment gas supply portion comprises a treatment gas supply hose connected to the treatment gas containment portion and each of said at least two electrodes are attached to the treatment gas supply hose by an insulated electrical conductor.

14. The apparatus of claim 13 wherein each of said insulated electrical conductors comprises an electrical plug at a supply end of the electrical conductor attached to the treatment gas supply hose.

15. The apparatus of claim 10, wherein the treatment gas containment portion further comprises:
  a seal gasket comprising a lower gasket peripheral portion adapted for attachment to the skin portion surrounding the wound and an upper gasket peripheral portion;
  a dome having a lower seal surface adapted to be removable and re-sealable with the upper gasket peripheral portion.

16. The apparatus of claim 15, wherein the lower gasket peripheral portion comprises a degradable adhesive.

17. The apparatus of claim 15, further comprising a means for sealingly and removeably attaching the lower seal surface to the upper gasket peripheral portion.

18. The apparatus of claim 15, further comprising a tab attached to the dome.

19. A method for treating a wound with a wound treatment apparatus, the treatment apparatus comprising a treatment gas applicator and at least two electrodes, each of said two electrodes connected to the treatment gas applicator by an insulated electrical conductor of predetermined length, the method comprising the steps:
  attaching the treatment gas applicator to a first skin portion surrounding the wound;
  attaching said at least two electrodes on a second skin portion adjacent to the first skin portion; and
  providing treatment gas to the treatment gas applicator and electrical current to said at least two electrodes in a predetermined sequence and time period.

20. The method of claim 19 wherein an attachment position of each of said at least two electrodes is spaced within the second skin portion as determined by the predetermined length of the electrical conductor.

21. treatment gas application apparatus for a wound comprising:
  an inflatable dome comprising an interior portion made of a flexible membrane and a peripheral portion, the peripheral portion comprising a first seal surface;
  a generally ring-shaped seal gasket comprising an upper gasket peripheral portion and a lower gasket peripheral portion, the upper gasket peripheral portion comprising a second seal surface sealable, removable and re-sealable with the first seal surface;
  a treatment gas supply fitting attached to the inflatable dome; and
  at least one exhaust vent in the inflatable dome;
  wherein the inflatable dome and the seal gasket define a treatment gas ventilated space surrounding the wound when the lower gasket peripheral portion is attached to the surrounding skin and the first seal surface of the inflatable dome is sealed to the second seal surface of the seal gasket.

22. The apparatus of claim 21 wherein the first seal surface comprises a contact adhesive.

23. The apparatus of claim 21 wherein the second seal surface comprises a contact adhesive.

24. The apparatus of claim 21 wherein the age-degradable adhesive comprises a hydrocolloid.

25. The apparatus of claim 21, wherein the lower gasket peripheral portion comprises an age-degradable adhesive, and wherein the lower gasket peripheral portion is adapted for attachment to the surrounding skin by the age-degradable adhesive.

26. The apparatus of claim 21, further comprising a filter disposed in the at least one exhaust vent.

27. The apparatus of claim 21, further comprising a tab attached to the inflatable dome peripheral portion.

28. A method for treating a wound comprising the steps of:
  providing a gasket having a lower gasket peripheral portion adapted for attachment to a skin portion surrounding a wound and having an upper gasket peripheral portion;
  providing a treatment gas containment having a lower seal surface adapted for attachment to the upper gasket peripheral portion;
  attaching the lower gasket peripheral portion to the skin portion surrounding a wound with a degradable adhesive;
  attaching the treatment gas containment lower seal surface to the upper gasket peripheral portion with a releasable and re-sealable contact adhesive;
  introducing a treatment gas into the treatment gas containment for treatment of the wound;
  removing the treatment gas containment lower seal surface from the upper gasket peripheral portion without removing the lower gasket peripheral portion from the skin portion surrounding the wound to provide access to the wound; and
  re-attaching the treatment gas containment lower seal surface to the upper gasket peripheral portion.

29. The method of claim 28, further comprising the steps of:
  attaching at least two electrodes at a predetermined length from the treatment gas containment;
  attaching the at least two electrodes to the skin surrounding the wound within the predetermined length from the treatment gas containment;
  connecting the at least two electrodes to a power supply;
  operating the power supply to stimulate the skin surrounding the wound during the step of introducing a treatment gas.

* * * * *